(12) United States Patent
Sharma

(10) Patent No.: US 7,392,082 B2
(45) Date of Patent: Jun. 24, 2008

(54) INTER-EPISODE IMPLEMENTATION OF CLOSED LOOP ATP

(75) Inventor: Vinod Sharma, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 445 days.

(21) Appl. No.: 10/672,229

(22) Filed: Sep. 26, 2003

(65) Prior Publication Data

US 2005/0070966 A1 Mar. 31, 2005

(51) Int. Cl.
*A61N 1/378* (2006.01)
(52) U.S. Cl. .......................................... 607/14
(58) Field of Classification Search ............. 607/14–15; 600/518
See application file for complete search history.

(56) References Cited

U.S. PATENT DOCUMENTS

| | | | | |
|---|---|---|---|---|
| 4,312,356 | A * | 1/1982 | Sowton et al. ................. | 607/14 |
| 6,167,308 | A | 12/2000 | DeGroot ....................... | 607/14 |
| 6,393,316 | B1 | 5/2002 | Gillberg et al. ............. | 600/515 |
| 6,400,986 | B1 * | 6/2002 | Sun et al. ...................... | 607/14 |
| 6,775,572 | B2 * | 8/2004 | Zhu et al. ...................... | 607/14 |
| 2004/0106956 | A1 | 6/2004 | Sharma et al. ................. | 607/9 |

OTHER PUBLICATIONS

Callans et al, "Characterization of Return Cycle Responses Predictive of Successful Pacing-Mediated Termination of Ventricular Tachycardia," *JACC*, vol. 25, No. 1, p. 47-53 (Jan. 1995).
Callans et al., "Characterization of Return Cycle Responses Predictive of Successful Pacing-Mediated Termination of Ventricular Tachycardia," *PACE (NASPE Abstracts)*, vol. 16, pt. II, p. 889 (Apr. 1993).

* cited by examiner

*Primary Examiner*—Carl H. Layno
*Assistant Examiner*—Frances P Oropeza
(74) *Attorney, Agent, or Firm*—Michael C. Soldner

(57) ABSTRACT

Improved methods and apparatus for providing optimal anti-tachycardia pacing (ATP) regimens in response to the return cycle length (RCL) exhibited by an exploratory ATP sequence initially applied upon detection of the tachycardia episode are disclosed. When a tachycardia episode is detected, an exploratory ATP sequence comprising a burst of pacing pulses is delivered, and an exploratory RCL is measured following delivery of the exploratory ATP sequence. A database of successful and unsuccessful ATP regimens associated with stored exploratory RCL values. The measured exploratory RCL and database are utilized to formulate an ATP regimen that is more likely than not to convert the tachycardia episode to NSR.

37 Claims, 6 Drawing Sheets

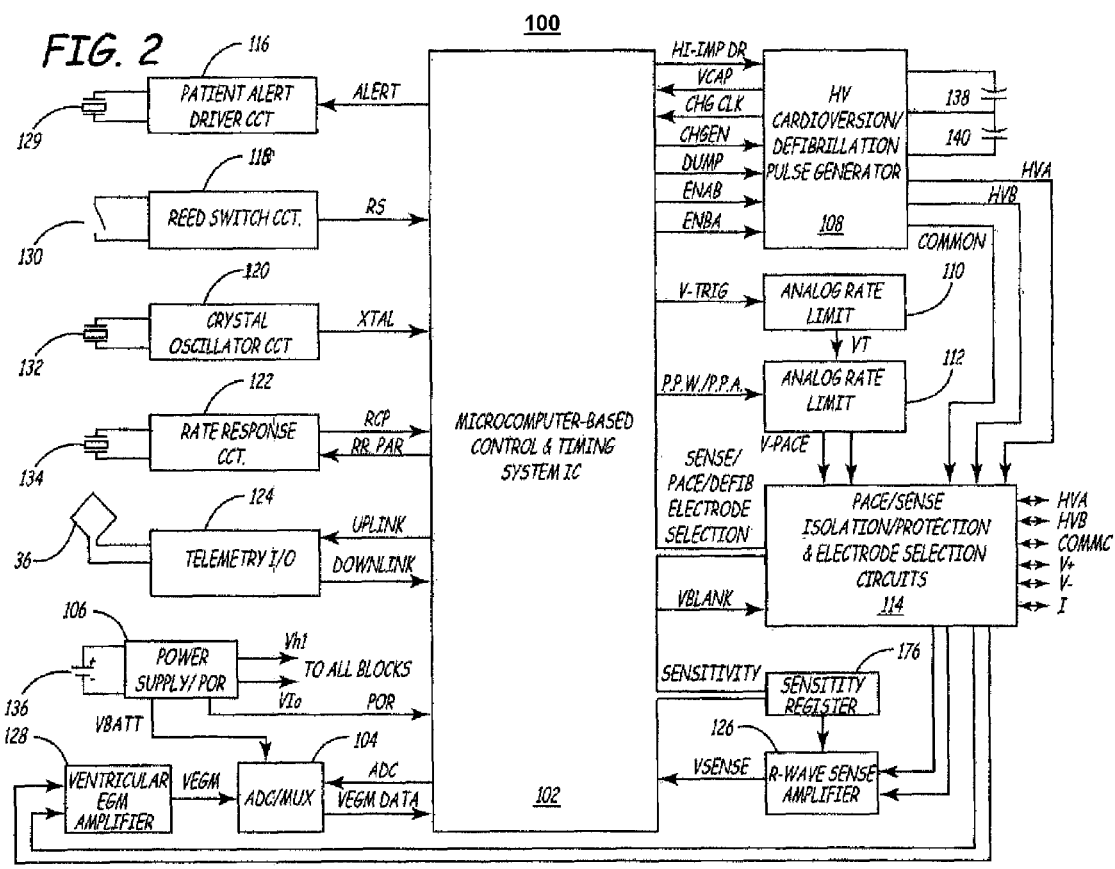

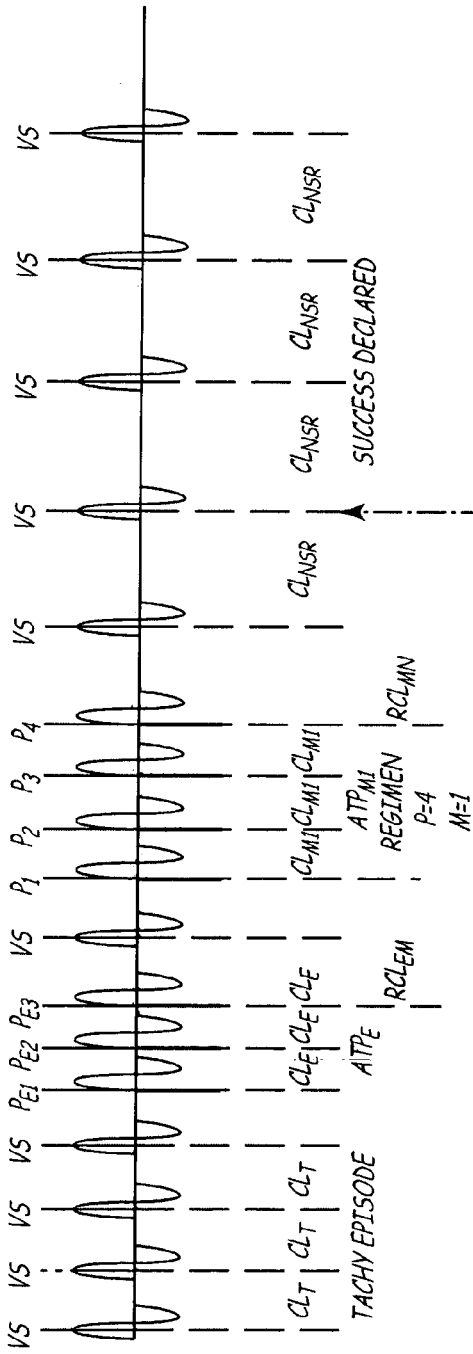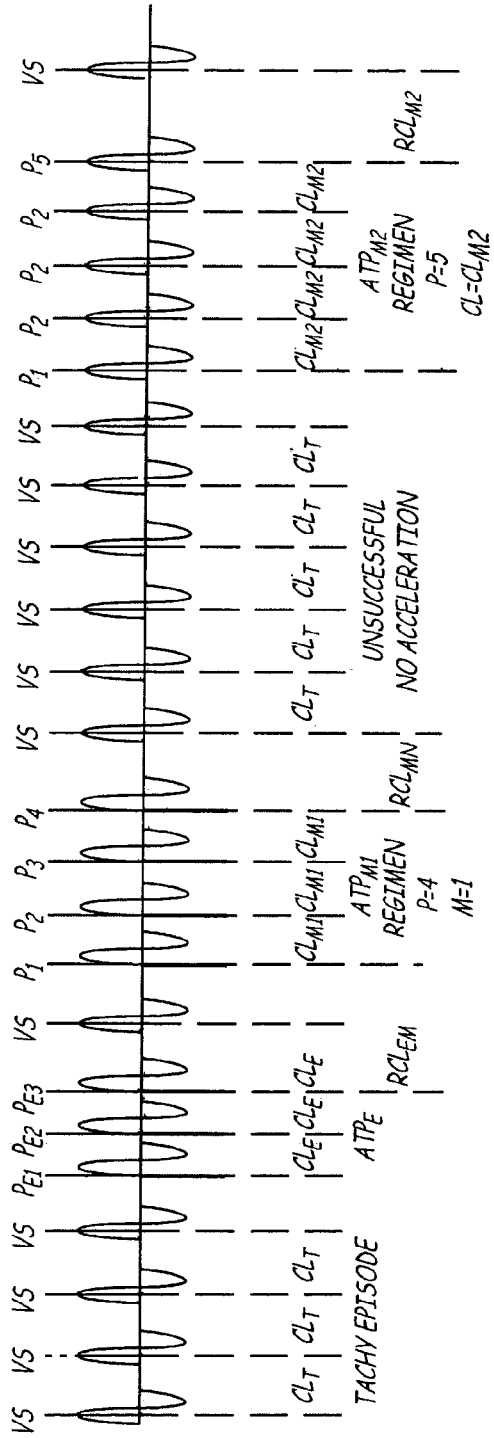

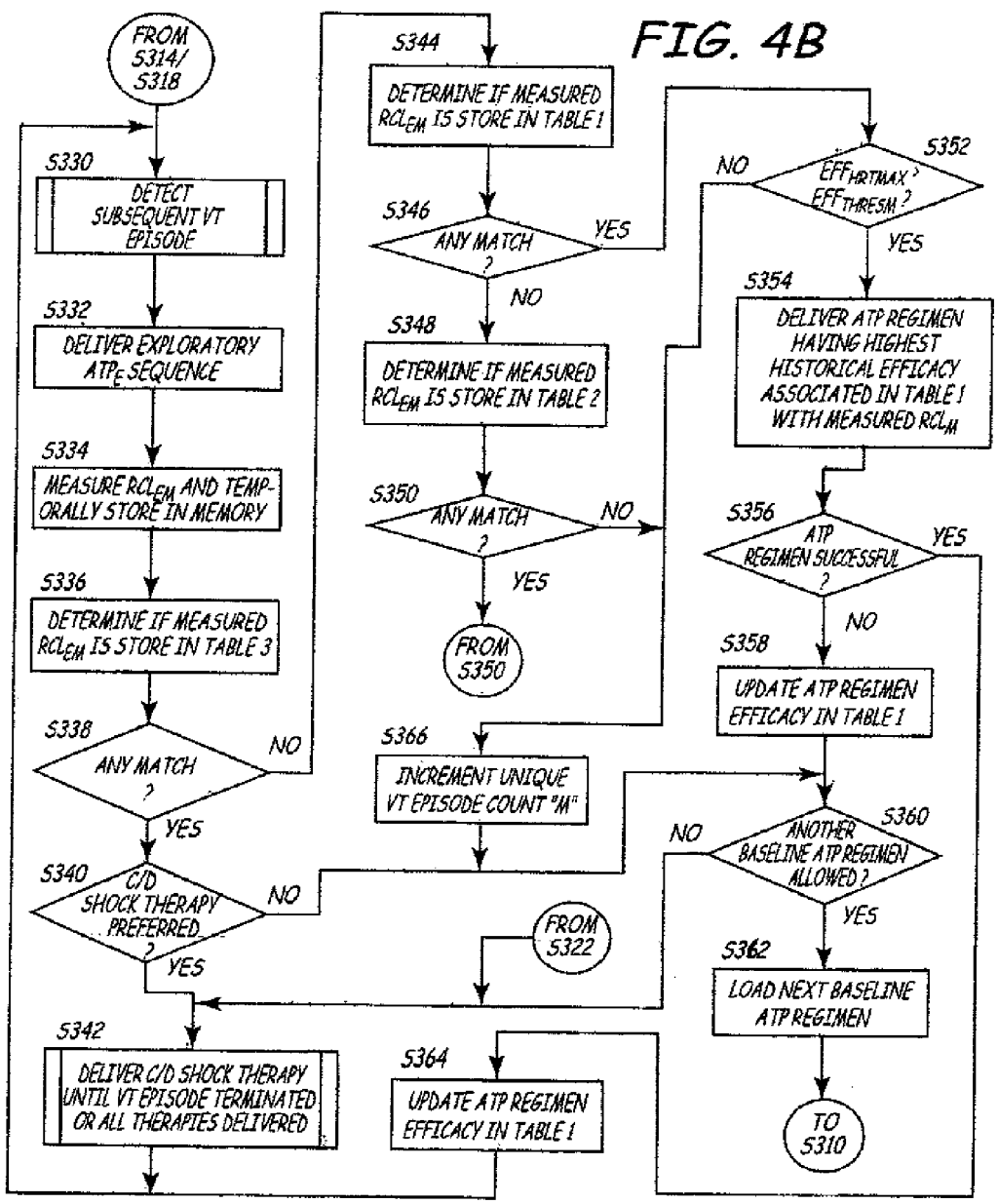

FIG. 5

LOOK-UP FOR TABLE 1 (ATP SUCCESS)

| $RCL_E$ FOR EXPLORATORY ATP SEQUENCE | ATP PARAMETERS OF SUCCESSFUL ATP REGIMEN | ATP HISTORICAL EFFICACY |
|---|---|---|
| $RCL_{E1}$ | PARAMETERS 1 | XX% |
| $RCL_{EM}$ | PARAMETERS 2 | YY% |
| ⋮ | ⋮ | |

LOOK-UP TABLE 2 (ATP FAILURE, NO ACCELERATION)

| $RCL_E$ FOR EXPLORATORY ATP SEQUENCE | $RCL_N$ FOR $(N-1)^{TH}$ ATP REGIMEN | $RCL_N$ FOR $(N-2)^{TH}$ ATP REGIMEN | ATP PARAMETERS FOR $(N-1)^{TH}$ FAILED ATP REGIMEN |
|---|---|---|---|
| $RCL_{E2}$ | $RCL_{2(N-1)}$ | $RCL_{2N}$ | PARAMETERS 1 |
| $RCL_{EM}$ | $RCL_{m(N-1)}$ | $RCL_{mN}$ | PARAMETERS 2 |
| ⋮ | | | ⋮ |

LOOK-UP TABLE 3 (ATP FAILURE, ACCELERATION)

| $RCL_E$ FOR EXPLORATORY SEQUENCE | $RCL_N$ FOR $N^{TH}$ ATP REGIMEN | $RCL_N$ FOR $N-1^{TH}$ ATP REGIMEN | ATP PARAMETERS FOR $N^{TH}$ ATP REGIMEN SEQUENCE THAT ACCELERATED |
|---|---|---|---|
| $RCL_{EM}$ | $RCL_{3(N-1)}$ | $RCL_{3N}$ | PARAMETERS 1 |
| $RCL_{EM}$ | $RCL_{m(N-1)}$ | $RCL_{mN}$ | PARAMETERS 2 |
| ⋮ | | | ⋮ |

INTER-EPISODE IMPLEMENTATION OF CLOSED LOOP ATP

FIELD OF THE INVENTION

This invention relates to implantable medical devices (IMDs), and more particularly to improved methods and apparatus for providing optimal anti-tachycardia pacing (ATP) regimens in response to the return cycle length (RCL) exhibited by an exploratory ATP sequence initially applied upon detection of the tachycardia episode.

BACKGROUND OF THE INVENTION

By way of definition, the term "tachyarrhythmia" refers to fast, abnormal rhythms of a heart chamber that include atrial flutter or fibrillation (AF) and ventricular flutter or fibrillation (VF), which may be amenable of conversion to a normal sinus rhythm (NSR) by "cardioversion" or "defibrillation", and tachycardias that may be amenable to conversion to NSR by the application of certain ATP regimens to the affected heart chamber. Such tachycardias include supra-ventricular tachycardia (SVT) originating from one or more ectopic site in the atria, and ventricular tachycardia (VT) originating from one or more ectopic site in the ventricles. Individuals whose heart's go from sinus rhythm into high rate, non-sinus rhythm described as atrial tachycardia(AT—a form of SVT) and VT can suffer debilitating physiologic effects that in certain cases can progress to more dangerous high rate VT or VF that lead to sudden cardiac death (SCD) unless the ventricles are cardioverted or defibrillated within a very short time after onset of such high rate VT or VF.

High rate, non-sinus, AT and VT episodes can often be terminated by the application of respective atrial and ventricular ATP regimens that comprise of train of pacing pulses delivered at a rate faster than the AT or VT rate. Each such train is referred to as an ATP sequence. A number of such ATP sequences in succession comprise a single ATP therapy and can be used to treat an AT or VT. However, efficacy of ATP regimens is not as high as the efficacy of alternative shock therapy, and hence there is always a chance that ATP may not be effective. To address this risk, automatic implantable arrhythmia control devices, particularly implantable cardioverter/defibrillators (ICDs) that provide staged or tiered therapies always include cardioversion/defibrillation regimens following an ATP. Among the most important functions of ICDs are to sense cardiac signals comprising the P-wave and/or R-wave, to detect and correctly identify the particular tachyarrhythmia that is occurring as a function of meeting specific detection criteria, to supply an appropriate cardioversion/defibrillation or ATP burst pacing regimen, and to determine whether or not the supplied regimen was effective. Current ICDs employ tachyarrhythmia classification algorithms that generally characterize heart rates between 150 and 250 bpm as tachycardias that can be further differentiated by their EGM morphology as either monomorphic or polymorphic. Atrial or ventricular arrhythmias exhibiting heart rates above the upper AT or VT range are typically classified as AF or VF, respectively.

The atrial and ventricular ATP regimens when applied to the atria and/or the ventricles to counter and convert AT or VT episodes to normal sinus rates can be highly efficacious and provide the advantage of being painless in contrast to the shock therapy, which while being even more efficacious can be quite painful. Parameters of the ATP regimens, including the pacing pulse amplitude and pulse width, the number of pacing pulses delivered in a given ATP, the inter-pulse interval between the pacing pulses and the coupling interval between the detected atrial P-wave or ventricular R-wave and the first delivered ATP pulse are programmed by the attending physician in patient work-ups to determine effective parameter values.

Typically, a series of ATP regimens are programmed to be delivered in succession to address the scenario that initial ATP regimens may not necessarily be effective in terminating the AT or VT episode. A termination algorithm is invoked by the ICD operating system upon delivery of the last pacing pulse of an ATP burst, and the delivery of one or more progressively more "aggressive" ATP burst regimens e.g., having an increased number of pace pulses and/or reduced inter-pulse interval, can be delivered depending upon the pre-programmed sequence. Typically, termination is confirmed by a return to NSR defined as a sequence of a predetermined number of spontaneous depolarizations (P-waves or R-waves) separated by greater than a defined interval.

Such an ICD providing burst ATP regimens is disclosed in commonly assigned U.S. Pat. No. 6,167,308 that is directed to an ICD or implantable anti-tachycardia pacemaker that modifies the ATP regimen for subsequent deliveries based on history, and which when continued in its original configuration would be unlikely to terminate the detected tachycardia.

As set forth in the article, "Characterization of return cycle responses predictive of successful pacing-mediated termination of ventricular tachycardia" by Callans et al, published in the *Journal of the American College of Cardiology*, Vol. 25, No. 1, January, 1995, pp 47-53, the pattern of return cycle length (the time period between the last pulse of an ATP and the first spontaneous depolarization detected post-ATP) for a series of ATP sequences can be predictive of the likelihood of success of a longer series of overdrive pacing pulses having the same parameters.

In the above-referenced '308 patent an ICD switches from a first programmed ATP regimen to a second programmed ATP regimen if the return cycle length (RCL) indicate that the ATP regimen being delivered is unlikely to be successful in terminating the tachycardia. In order to accomplish this result, an initial short series of pacing pulses of an ATP regimen are delivered, for example two to four pacing pulses, and delivery is then interrupted to measure the RCL. A second sequence of slightly different ATP regimen is then delivered, for example an ATP with one pulse incremented, and delivery is again interrupted to measure the RCL.

The second measured RCL would be expected to exceed the first measured RCL by a threshold amount if the burst pacing pulses were interacting with VT wavefront in a way that the conversion of AT or VT to NSR was likely. In that case, the aggressiveness (i.e. cycle length (CL) or inter-pulse interval) is maintained the same as the previously delivered ATP and a few more pulses are added to the subsequently delivered ATP sequence. As described before, a termination algorithm is invoked after ATP delivery to determine if the delivered ATP regimen was successful or unsuccessful in converting the tachycardia episode to NSR.

By contrast, it is presumed that the aggressiveness of the ATP regimen, is not sufficient to interact appropriately with the AT or VT and terminate the episode if the second measured RCL does not exceed the first measured RCL by a threshold amount, and the next programmed ATP therapy is typically more aggressive but has the same number of pulses as the previous ATP. If the ATP aggressiveness exceeds a pre-assigned threshold, no more ATP sequences are delivered for safety reasons and a cardioversion shock is delivered to terminate the episode.

This approach advantageously attempts to deliver an optimally aggressive ATP regimen. An optimal aggressiveness for the delivered ATP presumably can result in overall higher efficacy of ATP because it is presumed that an overaggressive ATP with empirically determined number of pulses can re-induce AT or VT that has been successfully terminated by the same ATP (e.g. initial pulses can terminate the tachycardia but later pulses might start it).

BRIEF SUMMARY OF THE INVENTION

In accordance with the present invention, when a tachycardia episode is detected, an exploratory ATP sequence comprising a burst of pacing pulses is delivered, and an exploratory RCL is measured following delivery of the exploratory ATP sequence. The measured exploratory RCL is utilized to formulate an ATP regimen that is more likely than not to convert the tachycardia episode to NSR.

The ATP regimen post-delivery RCL is measured and the success or failure of an applied ATP regimen is determined following delivery of each ATP regimen. A database storing successful and unsuccessful ATP regimens correlated with the measured exploratory RCL is developed as ATP regimens are delivered over time in response to successive tachycardia episodes. Each currently measured exploratory RCL is compared to the stored exploratory RCLs. A successful ATP regimen is selected if a match is made between the current measured exploratory RCL and a stored exploratory RCL associated with a stored successful ATP regimen. Preferably, an ATP regimen stored in the database in association with a particular exploratory RCL is characterized as successful if success is determined at least once, and an historical efficacy is also accumulated and stored in association with each successful ATP regimen. Preferably, the stored ATP regimen that has the highest historical efficacy is selected.

Upon implantation, the database of successful and unsuccessful ATP regimens associated with the exploratory RCL measured upon delivery of the exploratory ATP regimen is undeveloped, and one or more physician programmed baseline ATP regimen is followed. Thus, the formulation of the ATP regimen involves simply employing the baseline ATP regimen in the absence of stored ATP regimens associated with exploratory RCLs matching the measured exploratory RCL. The success or failure of each baseline ATP regimen is determined, and the database of exploratory RCLs associated with the successful or unsuccessful ATP regimens is constructed.

In a one aspect of the invention, an iterative algorithm is enabled that alters the parameters of previously stored unsuccessful ATP regimens that did not accelerate the tachycardia rate within certain programmable limits. These unsuccessful ATP regimens can be the default or physician defined baseline therapies in their original form or modified version of the baseline therapies. If a delivered ATP regimen is unsuccessful but does not accelerate the tachycardia rate, the parameters (number of pulses and CL) for the ATP are stored along with the RCLs for the last two ATP regimens delivered. When a subsequent AT or VT episode with similar RCL signature (i.e. RCL to exploratory ATP sequence) is encountered, the ATP parameters for the last delivered ATP regimen are modified based on the corresponding RCL information to arrive at a new ATP regimen that would have greater likelihood of successfully terminating the AT or VT episode.

Additional data is added to the database with each VT episode and RCL determination. The data fall into three sub-categories and are stored separately. One set of data is for successful ATPs, which are stored along with the corresponding exploratory RCLs and historical efficacies for terminating VT of a particular RCL signature. The second set of data keeps track of all the unsuccessful but non-accelerating ATPs. When a subsequent episode with exploratory RCL belonging to this data set is encountered, the RCLs for previous two failed ATPs are used to arrive at parameters for the new ATP used to treat the detected ATP. The last set of data keeps track of ATPs that cause acceleration, and these are not delivered at least for the VT that was accelerated by that ATP during a previous attempt. In a further aspect of the invention, the accumulated databases can be accessed by the attending physician in subsequent telemetry session during a patient follow-up, so that the physician can adjust the ATP regimens.

Thus, advantageously the ATP regimens that are more likely to successfully terminate the tachycardia are rapidly accessed from the database and delivered, resulting in more efficacious therapy delivery that terminates the tachycardia earlier and more frequently, thereby reducing battery depletion and the need to deliver painful and energy consuming cardioversion/C/D shock therapies.

This summary of the invention has been presented here simply to point out some of the ways that the invention overcomes difficulties-presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 2 is a schematic block diagram of the circuitry of the ICD IPG of FIG. 1 in which the present invention may advantageously be practiced;

FIGS. 3A and 3B are timing diagrams exhibiting the detection of a VT episode and delivery of an exploratory sequence, measuring the RCL and delivery of an ATP regimen in accordance with the present invention;

FIGS. 4A and 4B constitute a flow chart illustrating one method of providing ATP regimens to terminate a detected tachycardia episode in accordance with the present invention; and FIG. 5 is the depiction of a database accumulated in accordance with the present invention employed in steps of the flow chart of method of FIGS. 4A and 4B.

DETAILED DESCRIPTION OF THE PREFERRED EMBODIMENTS OF THE INVENTION

In the following detailed description, references are made to illustrative embodiments of methods and apparatus for carrying out the invention. It is understood that other embodiments can be utilized without departing from the scope of the invention. In particular, the present invention is described in the context of a single chamber, ventricular ICD for providing the functions of monitoring the ventricular EGM, detecting VF, SVT, and VF, discriminating VF from VT and SVT, and providing ventricular ATP regimens in response to a detected VT episode, storing data related to detected VF, VT and SVT episodes for uplink telemetry transmission to external medical devices, and optionally providing VVI pacing for bradycardia.

Figure 1:
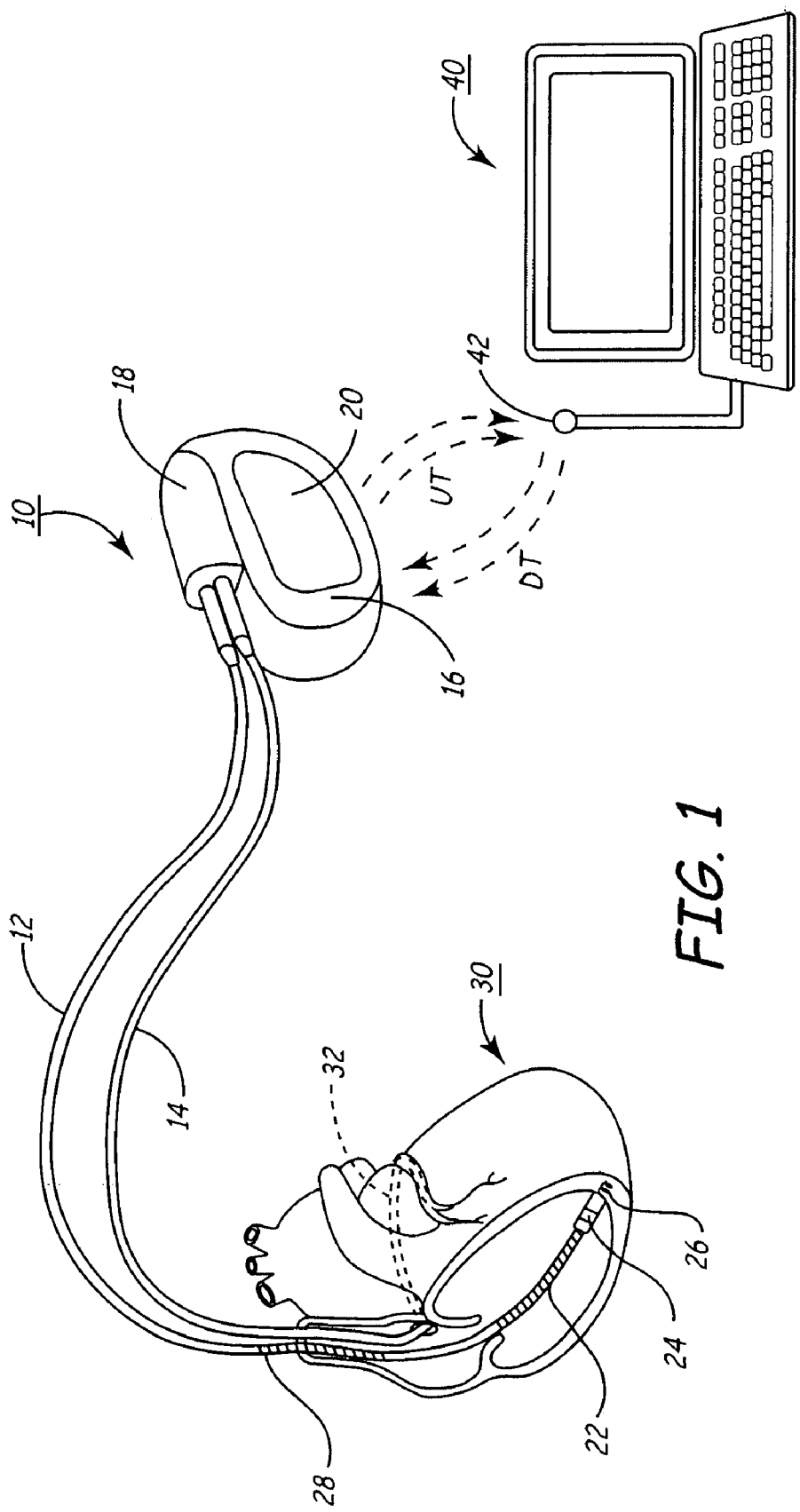
FIG. 1 is a schematic illustration of an ICD IPG and associated ICD leads extending from the ICD IPG to cardioversion/defibrillation and pace/sense electrodes located in operative relation to the ventricles of a heart.

FIG. 1 illustrates one embodiment of an ICD of the type disclosed in commonly assigned U.S. Pat. No. 6,393,316, comprising an ICD implantable pulse generator (IPG) 10 in which the ATP delivery algorithms of the present invention can be advantageously incorporated and the associated ICD medical electrical leads 12 and 14 extending to a human heart 30. The ICD of FIG. 1 is also shown in relation to an external programmer 40 and external programmer telemetry antenna 42 providing uplink telemetry (UT) and downlink telemetry (DT) transmissions with an IPG antenna.

The ICD IPG 10 is formed of a hermetically sealed enclosure 16 containing the electronic circuitry and components, including a battery, depicted in FIG. 2 and a connector block 18. The proximal ends of the illustrated ICD leads 12 and 14 are inserted into two connector ports of the connector block 18 to make electrical connections between lead conductors of the ICD leads 12 and 14 and the circuitry within the hermetically sealed enclosure 16 via feedthroughs extending through the enclosure wall in a manner well known in the art. The ICD IPG 10 is intended to be implanted subcutaneously remote from the heart, and at least an uninsulated portion of the hermetically sealed enclosure 16 may be employed as an indifferent pace/sense and/or cardioversion/defibrillation electrode 20.

The ICD lead 14 is a coronary sinus (CS) lead and the ICD lead 12 is a right ventricular (RV) lead and are extended transvenously from the ICD IPG 10 into the heart chambers using conventional implantation techniques. CS lead 14 supports an elongated wire coil, cardioversion/defibrillation electrode 32 that is located in the coronary sinus and great vein region of the heart 30. The cardioversion/defibrillation electrode 32 is advanced through the coronary sinus ostium in the right atrium and around the heart, and is disposed in proximity with the left ventricular wall either in the great vein or in the coronary sinus.

The RV lead 12 supports proximal and distal, elongated wire coil, cardioversion/defibrillation electrodes 22 and 28, a ring-shaped pace/sense electrode 24, and a helical pace/sense electrode 26 comprising an active fixation helix. The helical pace/sense electrode 26 is screwed into the tissue of the right ventricle at the right ventricular apex to fix the pace/sense electrodes 24 and 26 in the right ventricle. Other RV fixation mechanisms well known in the art, e.g., soft, pliant tines, may be substituted for the active fixation helix.

The cardioversion/defibrillation electrodes 22 and 28 are disposed in the RV and superior vena cava (SVC), respectively, to define one cardioversion/defibrillation vector between the base and apex of the heart 30. An RV-LV cardioversion/defibrillation vector is defined between the cardioversion/defibrillation electrodes 22 and 32. Other cardioversion/defibrillation vectors can be defined between the subcutaneous housing electrode 20 and any of the cardioversion/defibrillation electrodes 22, 28 and 32. Pairs of the cardioversion/defibrillation electrodes 22, 28 and 32 can be selectively coupled together to define further cardioversion/defibrillation vectors in a manner known in the art.

In conjunction with the present invention, the illustrated ICD leads and described electrodes are merely exemplary of possible lead systems and electrodes that can be paired together to detect R-waves, to process the EGM, to deliver C/D shocks in response to a confirmed VF detection, and to provide pacing, particularly to the right ventricle. The illustrated ICD leads and electrodes provide a variety of sense electrodes that can be paired and coupled to a ventricular sense amplifier to detect R-waves, an EGM amplifier to sense the EGM, and to a C/D shock generator to deliver monophasic or biphasic C/D shocks to the heart to counter VF. It will be understood that other ICD leads and pace/sense and cardioversion/defibrillation electrodes can be employed in the practice of the invention as long as the electrodes provide sense electrode pairs for detection of R-waves, for sensing the EGM, and for delivering the monophasic or biphasic C/D shocks to the heart to counter VF.

For example, in the simplest case of a low cost, limited function, prophylactic ICD, the ICD leads may comprise a simpler RV lead supporting only the cardioversion/defibrillation electrode 22 and a single distal pace/sense electrode. A high-energy monophasic C/D shock can be delivered between the cardioversion/defibrillation electrode 22 and the housing cardioversion/defibrillation electrode 20. The R-waves and the EGM can be sensed between the single distal pace/sense electrode and one of the cardioversion/defibrillation electrode 22 and the subcutaneous housing electrode 20. RV pacing during bradycardia may or may not be provided between the single distal pace/sense electrode and one of the cardioversion/defibrillation electrode 22 and the subcutaneous housing electrode 20.

Returning to FIG. 1, the ring electrode 24 and tip electrode 26 may be paired together and coupled to an R-wave sense amplifier to detect the occurrence of an R-wave, and ring electrode 24 and subcutaneous housing electrode 20 or one of the cardioversion/defibrillation electrodes 22, 28 and 32 may be paired together for sensing the EGM signal. Alternatively, pace/sense electrodes 24 and 26 may be used for both R-wave detection and EGM sensing. Moreover, two of the cardioversion/defibrillation electrodes 32, 22 and 28 may be paired together for sensing the EGM signal.

The ICD IPG 10 preferably comprises an ICD operating system as depicted in FIG. 2 that provides the operating modes and functions of the MEDTRONIC® GEM 7227 single chamber ICD IPG, for example, that is programmable in operating mode and parameter values and interrogatable employing the MEDTRONIC® Model 9790C external programmer 40. FIG. 2 is a functional block diagram illustrating such a single chamber ICD operating system 100 that is merely exemplary of a variety of single chamber and dual chamber ICD systems having all or some of the capabilities described above in which the VT/VF discrimination functions of the present invention can be advantageously implemented.

The programming of ICD operating modes and parameters or the interrogation of data stored in the ICD IPG 10 or the initiation of UT transmission of the real time cardiac EGM is accomplished or initiated via programming or interrogation commands transmitted in a DT transmission by programmer 40 from the external telemetry antenna 42 to an ICD telemetry antenna 36 shown in FIG. 2. In the context of the present invention, the ICD operating system stores VT/VF detection episode data and VT/VF therapy delivery data that can be UT transmitted to the external programmer 40 for review by a physician. The ICD IPG telemetry system decodes the commands in the DT transmission, retrieves and formats the responsive data or cardiac EGM and conveys it to the external programmer 40 as an UT transmission in any of the manners known in the art.

The ICD system 100 includes one of more ICs typically mounted on one or more hybrid circuit, a PC board mounting a number of discrete components, and further large scale, discrete components. The heart of the ICD operating system is in hardware and software in the microcomputer based timing and control system IC 102 that is coupled with the other system blocks. The system IC 102 comprises the typical components of a microcomputer with operating algorithms maintained in memory or embedded in firmware and further operating system control circuitry that is conveniently located with it. Various depicted signal and control lines interconnecting these blocks, but not all are shown for simplicity of illustration and because they play no material role in the practice of the present invention.

The large-scale, discrete, off-board, components include one or more batteries 136, HV output capacitors 138, 140, and (optionally) housing mounted, patient alert sound transducers 129, coupled to patient alert driver circuitry 116, and/or activity sensors 134. The discrete components mounted to the PC board include telemetry antenna 36, reed switch 130 coupled to reed switch circuit 118, crystal 132 coupled to crystal oscillator circuit 120, a set of HV discrete components of the HV cardioversion/defibrillation output circuitry 108, and switching and protection circuit components of block 114. These discrete components are coupled to system IC 102 through other ICs and hybrid circuits incorporating the functional blocks 104-128 and 176 described further below. A similar ICD operating system to that depicted in FIG. 2 in which the present invention can be implemented is disclosed, for example, in the above-referenced '316 patent. The depicted functional blocks and discrete components of FIG. 2 can be arranged as part of one or two LV hybrid circuits, a HV hybrid circuit and a discrete component PC board. However, it will be understood that a single hybrid circuit could be employed that incorporates and supports all of the system ICs.

The exemplary ICD operating system 100 of FIG. 2 is powered by the battery 136 coupled to power supplies in power source block 106 for developing regulated high and low voltage power supplies Vhi and Vlo that are supplied to selected ones of the other functional blocks. Preferably, battery 136 is a lithium silver vanadium battery that can be employed to provide HV capacitor charging current and that produces a voltage from about 3.2 volts when fresh to about 2.5 volts at specified end of service for a single chamber ICD and twice these values for a dual chamber ICD. Power supply 106 also includes a power-on-reset (POR) circuit that generates a POR signal initially when the battery 136 is connected with power supply 106 and any time that the voltage of battery 136 falls below a threshold voltage.

The crystal oscillator circuit 120 is coupled to clock crystal 132 and provides one or more system XTAL clock that is applied to the microcomputer-based control and timing system IC and distributed to other blocks of FIG. 2 as appropriate.

The telemetry I/O circuit 124 coupled with the IPG telemetry antenna 36 includes a UT transmitter that receives formatted UPLINK signals for uplink transmission and a DT receiver that receives and forwards DOWNLINK signals to telemetry I/O registers and control circuitry in system IC 102. In one telemetry scheme known in the art, the telemetry I/O circuit 124 is enabled to receive and decode DT interrogation and programming commands when the reed switch circuit provides the RS signal upon closure of reed switch 130 by an external programming head magnetic field. Downlink telemetry RF signals ring an L-C tank circuit including the IPG telemetry antenna 36. Other pacing functions are also affected when a magnetic field closes the, reed switch 130 and the RS signal is generated in a manner well known in the art. In more recent telemetry schemes, the reed switch is not employed to receive DT transmissions, and the type of telemetry scheme employed in FIGS. 1 and 2 is not material to the present invention.

Optionally, a rate response circuit 122 is coupled to a physiologic activity sensor 134, which is preferably a transducer or accelerometer mounted to the IPG housing inner surface and provides activity correlated output signals to the rate response circuit 122 in a manner well known in the art. The rate response circuit 122 develops a rate control parameter (RCP) that is used to vary a pacing escape interval to pace the heart at a rate that provides adequate cardiac output. The signal processing of the transducer output signal by the rate response circuit 122 can be programmed through rate response parameter commands to develop the RCP in a number of ways known in the art. The RCP associated with a detected VT/VF episode can also be stored in memory in the system IC 102 for UT transmission of the episode data to the external programmer 40 for analysis by the patient's attending physician.

Optionally, a patient alert driver circuit 116 is coupled to a sound emitting transducer 129, which is mounted adjacent to the interior surface of the IPG housing and is powered to emit audible warning signals, in high urgency and low urgency tones to alert the patient of VF detection and imminent delivery of a C/D shock or of events or conditions of concern warranting physician intervention. The warnings that can be programmed into operation or programmed "off" include pace/sense and CVWDEFIB lead impedance out of range (too high or too low), low battery voltage, excessive charge time for charging the HV capacitors, all regimens in a programmed group of regimens delivered ATP either during that particular detection of that episode or during a later detection of the same VT (i.e. VT having same exploratory RCL signature).

The block diagram of FIG. 2 depicts six input/output terminals labeled V+, V−, I, HVA, HVB, and COMMC that represent the connector terminals within the IPG connector block 104 that can be coupled to lead connector elements and lead conductors extending to the respective electrodes 24, 26, 30, 22, 32, and 28. As noted above, the number of input/output terminals and associated electrodes can be reduced to the minimal number necessary to practice the present invention.

The pace/sense isolation/protection and lead impedance switch circuits 114 selectively couple pairs of the six input/output terminals labeled V+, V−, I, HVA, HVB, and COMMC to the R-wave sense amplifier 126, the ventricular EGM amplifier 128 and the V-PACE pulse generator 112 in response to a corresponding sense/pace electrode selection command from the microcomputer-based control and timing system IC 102. The sense/pace electrode selection command is programmable by the patient's attending physician through use of the external programmer 40 as described above.

A ventricular pacing function for bradycardia operating in any of the ways that are well known in the art may or may not be included in a low cost, limited-function prophylactic ICD as described above. The V-PACE generator 112 provides V-PACE pulses through the selected pace/sense electrode pair having a pulse width and pulse amplitude set by the programmed PPW/PPA commands in a VVI of VVIR pacing mode. A timer in the microcomputer-based control and timing system 102 times out a programmed VVI pacing escape interval or a VVIR pacing escape interval that varies as a function of the RCP output by the rate response circuit 122. A V-TRIG signal is generated by microcomputer-based control and timing system 102 when the VVI or VVIR escape interval times out and applied to the analog rate limit circuit 110, which inhibits erroneous triggering of pacing at an unacceptably high rate in a manner well known in the art. The acceptable V-TRIG signals are passed through the analog rate limit 110 and trigger the delivery of the V-PACE pulse by the V-PACE pulse generator 112. The VVI or VVIR escape interval is restarted by a VSENSE generated by the ventricular sense amplifier 126 in response to an R-wave.

Similarly, the microcomputer-based timing and control system 102 also generates the V-TRIG signals for each V-PACE pulse of each ATP regimen that is applied to the RV in response to a detected VT episode. The plurality of V-TRIG signals are provided separated by a cycle length (CL) defining the pacing rate. The V-PACE pulses of the ATP regimen have a pulse width and pulse amplitude set by the programmed PPW/PPA commands.

The V-PACE pulse generator 112 can be coupled in response to a programming command through the pace/sense isolation/protection and lead impedance switch circuits 114 to the V+, V− input/output terminals to be thereby coupled with the pace/sense electrodes 24 and 26 to provide bipolar RV pacing. Or, the V-PACE pulse generator 112 can be coupled through the pace/sense isolation/protection and lead impedance switch circuits 114 to the V− terminal to be thereby coupled with the pace/sense electrode 26 and any of the I, HVA, HVB, and COMMC input/output terminals to be thereby coupled with the respective electrodes 20, 22, 32, and 28 to provide unipolar RV pacing.

In one preferred example, the ventricular sense amplifier 126 is coupled through the pace/sense isolation/protection and lead impedance switch circuits 114 to the V+, V− terminals to be thereby coupled with the pace/sense electrodes 24 and 26 to provide bipolar RV sensing of R-waves. The inputs to the ventricular sense amplifier 126 are disconnected from the V+, V− terminals by the pace/sense isolation/protection and lead impedance switch circuits 114 in response to and for the duration of a VBLANK signal generated by a ventricular blanking circuit in microcomputer-based control and timing system IC 102 upon delivery of a V-PACE pulse or a C/D shock.

The ventricular sense amplifier 126 comprises a programmable gain, bandpass amplifier, a threshold setting circuit, and a comparator for comparing the bandpass filtered ventricular cardiac signal amplitude to the threshold. The sensing threshold of the ventricular sense amplifier 126 stored in sensitivity register 176 is programmable by the patient's attending physician through use of the external programmer 40 as described above. The ventricular sense amplifier 126 generates the VSENSE signal when it is not blanked and the amplitude of QRS complex exceeds the ventricular sensing threshold, which is typically during the rise of the R-wave.

Similarly, the ventricular EGM (VEGM) amplifier 128 is coupled through the pace/sense isolation/protection and lead impedance switch circuits 114 in response to a programmable VEGM vector electrode selection command to a pair of the input/output terminals selected from input/output terminals V+, V−, I, HVA, HVB, and COMMC. The VEGM amplifier 128 filters and amplifies the cardiac signals and provides the VEGM signals to ADC/MUX 104. In the ADC/MUX 104, the VEGM is continually sampled at a sampling frequency of 256 Hz, and the sampled analog signal values are digitized and provided as VEGM DATA to RAM memory registers or buffers in system IC 102 for temporary storage on a FIFO basis. The temporarily stored VEGM DATA are shifted into memory registers within system IC 102 when a tachyarrhythmia episode satisfying the VT or VF rate detection and other detection criterion is detected.

VEGM DATA can be stored for retrieval in an UT transmission in memory registers to provide programmable length VEGM strips preceding and following the detection of the arrhythmia and encompassing any delivery of a C/D shock. Due to memory limitations, the stored VEGM DATA may be discarded and replaced each time a VT/VF episode is detected. However, historic episode logs can be compiled and incremented in RAM in system IC 102 that provide the date, time, type of episode, cycle length, duration, and identify the last stored EGM DATA.

The depicted HV cardioversion/defibrillation output circuit 108 is of the type described in the above-incorporated '316 patent comprising a DC-DC converter and a HV output or discharge circuit for discharging the charge on the HV output capacitor bank 138 and 140 through selected ones of the cardioversion/defibrillation electrodes 22, 28, 32 and 20 of FIG. 1. The DC-DC converter comprises a HV charging circuit, a discrete HV step-up transformer, and the HV output capacitor bank 138 and 140 coupled to the secondary transformer coils. The charge on the HV output capacitor bank 138 and 140, in this case, is selectively discharged through combinations of the leads coupled with the cardioversion/defibrillation electrodes 26, 30 and 32 of FIG. 1 via HV switches in the switch circuit block 114. In a prophylactic ICD of the type described above, the depicted HV cardioversion/defibrillation output circuit 108 develops a high-energy monophasic or biphasic C/D shock that is delivered through a selected pair of the cardioversion/defibrillation electrodes 26, 30 and 32 of FIG. 1 via the HV switches in the switch circuit block 114.

The microprocessor within the microcomputer-based control and timing system 102 operates as an interrupt driven device, under control of software stored in ROM associated with microprocessor and responds to interrupts including the VSENSE output of the R-wave sense amplifier 126 and the time-out of the VVI or VVIR escape interval. Any necessary mathematical calculations to be performed by the microprocessor and any updating of the values or intervals controlled by pacer timing/control circuitry within the microcomputer-based control and timing system 102 take place following such interrupts.

As described in the above-referenced '316 patent, the typical VT/VF detection algorithms that have been employed in commercially released ICDs of the type illustrated in FIGS. 1 and 2 employ rate/interval based timing criteria as a basic mechanism for detecting the presence of and distinguishing between tachyarrhythmias. A similar scheme is used for detecting the presence of atrial tachyarrhythmias. Below we will describe the device operation for an ventricular chamber but it should kept in mind that the operation can generally be extended to the atrial chamber by making appropriate replacements in the text e.g. P-wave for R-wave, AT for VT, AF for VF etc. Towards the goal of detecting an episode, the intrinsic heart rate is measured on a beat-to-beat basis by timing the R-R interval between successive VSENSE signals output by the R-wave sense amplifier 126. The R-R interval is compared to the interval ranges established, typically by programming, for each of VF, high rate VT, and low rate VT. The count of a corresponding VF counter, high rate VT counter, or low rate VT counter is incremented.

For example, the R-R interval is simultaneously compared to a programmed fibrillation detection interval (FDI), a programmed high rate or fast tachycardia interval (FTI), and a programmed low rate tachycardia detection interval (TDI). An FDI count is incremented if the R-R interval is shorter than the FDI. A low rate VT count is incremented in response to an R-R interval shorter than TDI but longer then the FTI or the FDI. A high rate VT count is incremented in response to an R-R interval longer than FDI but shorter than the FTDI. In algorithms that employ all three rate ranges, it is suggested that a QRS width criterion be employed only in conjunction with classification of R-R intervals falling between TDI and FTDI.

The counts accumulating in the respective counters may be used to signal detection of an associated arrhythmia (VF, fast VT, or slow VT) when they individually or in combination reach a predetermined value, referred to herein as "NID" (number of intervals required for detection). Each rate zone may have its own defined count and NID, for example "VFNID" for fibrillation detection and "VTNID" for VT detection or combined counts may be employed. These counts, along with other stored information reflective of the previous series of R-R intervals such as information regarding the rapidity of onset of the detected short R-R intervals, the stability of the detected R-R intervals, the duration of continued detection of short R-R intervals, the average R-R interval duration and information derived from analysis of stored EMG segments are used to determine whether tachyarrhythmias are present and to distinguish between different types of tachyarrhythmias.

In ICDs having dual chamber, atrial and ventricular, sensing capabilities, other strategies have been generally followed to detect and classify tachyarrhythmias that start with identifying atrial sensed events from P-waves and/or ventricular sensed events from R-waves and deriving atrial and/or ventricular event intervals and/or rates therefrom. In both single and dual chamber ICDs, VF has been typically detected based strictly on ventricular heart rate (or R-R interval) while VT has been detected based on ventricular heart rate along with other parameters, e.g., sudden onset, rate stability, and sensed physiological activity (exercise). For example, the R-R event intervals are compared to programmed FDI ranges and TDI ranges and to suddenness of onset criteria and rate variability criteria to distinguish various tachyarrhythmias from one another.

For purposes of the present invention, the particular details of implementation of the rate/interval based VT detection methodologies are not of primary importance. The present invention is practiced in the context of this exemplary ventricular ICD embodiment when VT detection criterion are met and a sequence of ATP regimens are programmed to be delivered to the RV to convert the VT to NSR. It will be understood that the present invention may also be practiced in the context of ventricular single and dual chamber anti-tachycardia pacemakers, dual chamber ICDs, and in atrial or dual chamber ICDs and atrial or dual chamber anti-tachycardia pacemakers for conversion of atrial tachycardia (AT) episodes.

As described further below, it would be expected that the attending physician would program a fixed number of "N" ATP regimens that can be delivered in response to any single detected VT episode before one or more cardioversion/defibrillation (C/D) shock therapy is delivered and all ATP therapies are exhausted. Such physician programmed ATP regimens are characterized herein as "baseline" ATP regimens. It will be understood that the number "n" is used in the figures and the following discussion to signify the current ATP regimen (or sequence) number from the N number of ATP regimens delivered to any given ATP. Initially, the N ATP regimens will be the physician programmed ATP regimens, but as VT episodes are detected the ATP regimens that are actually delivered will evolve as the database is developed to comprise those determined to be most likely to terminate the VT episode based on the RCL in response to a exploratory ATP sequence $RCL_{Em}$ (where suffix m keeps track of the distinct number of VT episodes; see below). Therefore the last ATP regimen to be delivered is numbered "N", and the preceding delivered ATP regimens are numbered n="N−1", N−2", ... "N−(N−1)". For example, if N=3, then the first delivered ATP regimen is designated n="N−2" or "1", the second delivered ATP regimen is designated n="N−1" or "2" and the third delivered ATP regimen is designated "N" or "3". The cycle lengths of the pacing pulses of each delivered ATP regimen are also designated "$CL_N$", "$CL_{N-1}$", etc.

A VT episode count "m" is also maintained that is incremented whenever a unique VT episode marked by a characteristic $RCL_{Em}$ is detected. The $RCL_{Em}$ and history of successful and unsuccessful ATP regimens delivered to this new VT are stored in one of the look-up Tables 1-3. In other words, the VT episode count "m" maintains the count of unique number of VTs encountered in the life of the device and is not incremented when a previously detected VT episode, as marked by a match between the currently measured exploratory $RCL_{Em}$ and an existing $RCL_{Em}$ in Tables 1-3, is encountered Therefore, in FIGS. 3-5, the symbol "n" appended to the various acronyms represents the number of the ATP regimen that is delivered in the course of responding to any detected VT episode, and the symbol "m" appended to the various variables represents the count of the VT episode. For example, the designation $RCL_{mn}$ signifies the RCL measured following delivery of the $n^{th}$ ATP regimen in the response to the $m^{th}$ unique VT episode. The designation $RCL_{Em}$ signifies the exploratory RCL for the $m^{th}$ counted VT episode. The designation $CL_{mn}$ signifies the cycle length of the $n^{th}$ delivered ATP regimen for the $m^{th}$ unique VT.

Figure 4A:
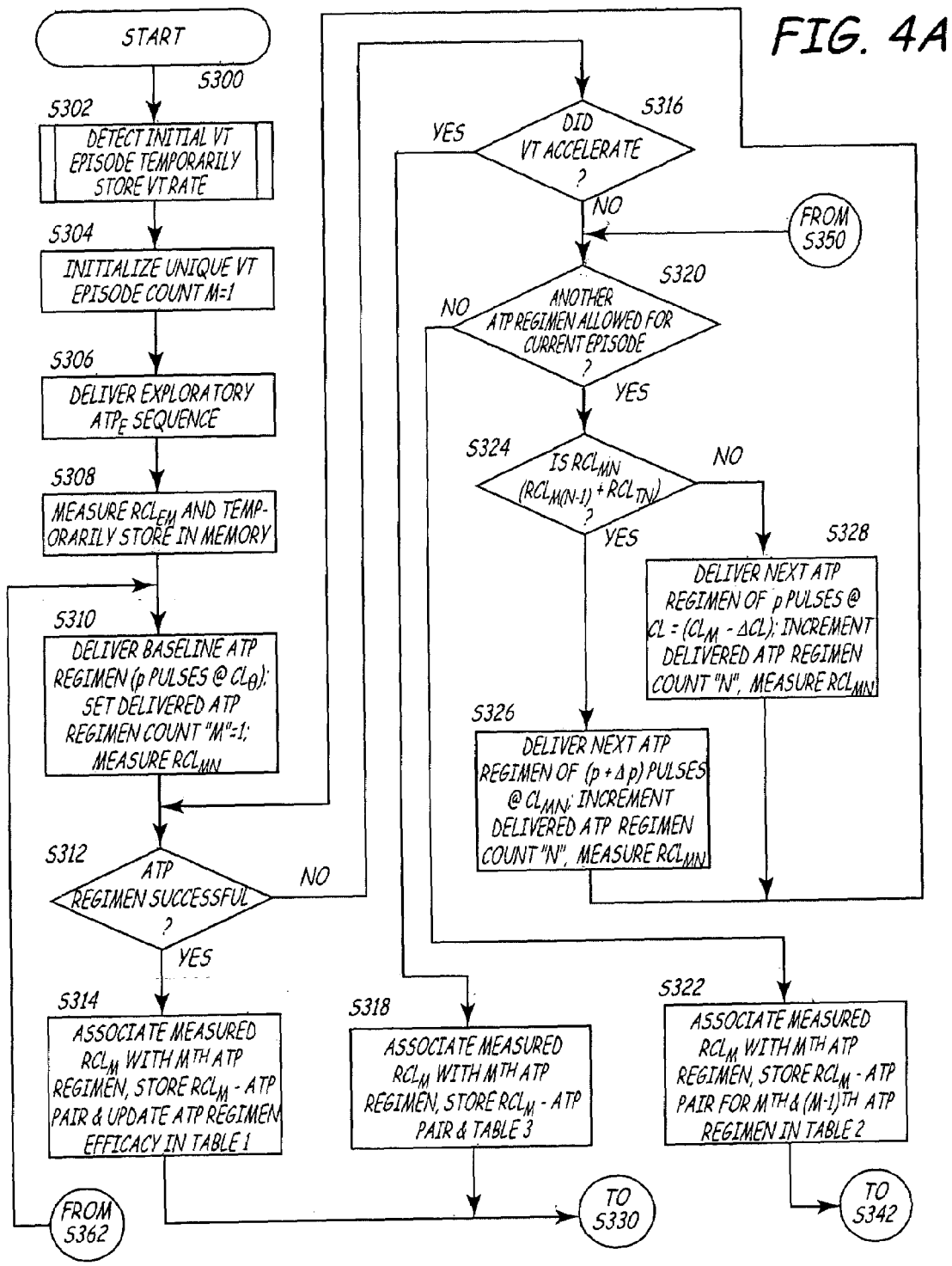

An iterative algorithm is depicted in FIGS. 4A and 4B that over the ICD lifetime develops the database depicted in the look-up Tables 1, 2, and 3 of FIG. 5. The database Tables 1, 2, and 3 of successful and unsuccessful ATP regimens correlated to the measured exploratory $RCL_{Em}$ depicted in FIG. 5 is developed over time starting with (and periodically reverting to) application of the physician programmed baseline ATP regimens, determination and database storage of their success or failure in terminating VT episodes, and delivering successive ones of the "N" ATP regimens with ATP parameters varied from the ATP parameters of the programmed baseline ATP regimens.

In accordance with this illustrated embodiment of the present invention, when a VT episode is detected, an exploratory ATP sequence of pacing pulses are applied and the exploratory $RCL_{Em}$ is measured. A VT episode number "m" is illustrated in FIGS. 3A and 3B that is characterized by a sequence of high rate, spontaneously occurring, R-waves detected from the VSENSE events (shortened to "VS" in FIGS. 3A and 3B) separated by intrinsic tachycardia cycle lengths $CL_T$. Such VT episodes are detected employing one of the above-described VT detection algorithms.

An exploratory $ATP_E$ sequence of P=3, in this example, exploratory pacing pulses, $P_{E1}$, $P_{E2}$, and $P_{E3}$ are delivered at a pulse energy that captures the ventricles and elicits pace triggered R-waves. The $ATP_E$ sequence is selected in number of $ATP_E$ pulses and the $ATP_E$ pacing rate, set by exploratory cycle length $CL_E$, to ensure that the intrinsic VT is overdriven or suppressed and that at least the last $ATP_E$ pacing pulse $P_{E3}$ is likely to interact with the VT circuit. However, these parameters (number P and cycle length $CL_E$) of the ATPE sequence are selected to not likely terminate the VT episode. The exploratory $RCL_{Em}$ is then measured from the last $ATP_E$ pacing pulse $P_{E3}$ to the VSENSE detection of the next intrinsic R-wave.

Referring again to FIG. 3A, the first (n=1) ATP regimen having P=4 pacing pulses and a cycle length $CL_{mn}$ is formulated by comparing the current measured $RCL_{Em}$ to the stored exploratory RCLs in Tables 1, 2 and 3 that store information regarding previously delivered successful and unsuccessful ATP regimens. A baseline ATP regimen can be delivered if the current measured $RCL_{Em}$ matches a stored exploratory RCL in look-up Table 3 or if there are no matches with any stored exploratory RCLs in any of look-up Tables 1 to 3. A "match" of the current exploratory RCL with one of the stored exploratory RCLs in Tables 1 to 3 is declared if any difference is within a certain defined tolerance, e.g. +/−10 ms, for example.

Generally speaking, the exploratory $RCL_E$ that is measured after delivery of the exploratory ATP sequence following detection of a VT episode is compared first to each stored exploratory RCL associated with a delivered ATP regimen in look-up Table 3, second to each stored exploratory RCL associated with a delivered ATP regimen in look-up Table 1, and third to each stored exploratory RCL associated with a delivered ATP regimen in look-up Table 2. The particular details of the comparisons are set forth below in reference to FIGS. 4A and 4B.

If the current measured exploratory RCL matches one of the exploratory RCL stored in Table 3 in association with unsuccessful ATP regimens causing acceleration of the VT rate, then none of the ATP regimens stored in Tables 1-3 are selected. A different baseline ATP regimen than the first previous detection of that episode or a C/D shock therapy is delivered instead.

A successful ATP regimen of Table 1 is selected to be delivered if: (1) it is correlated to a stored exploratory $RCL_{Em}$ in Table 1 that matches the current measured exploratory $RCL_{Em}$; and (2) it possesses a certain "ATP Historical Efficacy" that is also stored in Table 1 and updated depending upon a determination of success or failure each time that ATP regimen is formulated (selected) and delivered. When a match is found between the currently measured exploratory RCL and $RCL_{Em}$ stored in Table 1, but the corresponding ATP therapy is unsuccessful, a new successful ATP therapy may be constructed starting from a new baseline therapy and associated with the same $RCL_{Em}$. Thus, Table 1 may have more than one ATP regimens associated with VT episodes that exhibit the same (within the defined tolerances) measured exploratory RCL. However, it is also assumed that the Historical Efficacies of such stored ATP regimens will differ. Thus, in practice, the ATP regimen enjoying the highest Historical Efficacy will be preferentially selected and delivered if a match is made between the measured exploratory RCL and more than one stored $eRCL_{Em}s$ values in Table 1.

An ATP sequence is formulated in a manner described further below if there are no matches between the currently measured exploratory RCL and any of the $RCL_{Em}$ values stored in Tables 3 and 1, but a match is made with an $RCL_E$ value stored in Table 2.

Returning to FIG. 3A, it will be assumed that the measured exploratory RCL is utilized in one of the ways summarized above to formulate an ATP regimen comprising of "p" ATP pacing pulses, $P_1$ through $P_P$, each having a pulse energy likely to capture the heart at a pacing rate dictated by an overdrive cycle length $CL_{mn}$ (where "n" is 1st, 2nd or $N^{th}$ ATP therapy delivered following measurement of $RCL_{Em}$ of the $m^{th}$ VT episode). The n=1 ATP regimen is delivered, and $RCL_{m1}$ (i.e., n=1) is measured from the last ATP regimen pacing pulse $P_4$ to the VSENSE detection of the next intrinsic R-wave.

In the example depicted in FIG. 3A, the first delivered ATP regimen is determined to be successful in terminating the VT as evidenced by the measured intrinsic cycle lengths between the VSENSE events (designated $CL_{NSR}$) that are longer than a VT threshold cycle length. In this instance, the VT episode count "m" would be incremented and the delivered ATP regimen associated with the measured $RCL_{Em}$ would be stored in the look-up Table 1, if the combination is not already present in Table 1 If the combination is already stored in look-up Table 1, then the episode count "m" would not be incremented but the ATP Historical Efficacy for the particular ATP regimen would be increased, if less than 100%.

In FIG. 3B, the VT episode is not terminated by the first delivered ATP regimen as determined by the measurement and processing of the post-delivery VSENSE events and measurement and comparison of the intrinsic cycle lengths $CL_T$ to VT detection criterion. It is determined that the VT episode has not accelerated by comparison of the post-delivery $CL_T$ to the pre-delivery $CL_T$. It is also assumed that maximum number (N) of ATP therapies allowed to be delivered for a VT episode is set to be 2 so that a second ATP regimen is delivered for this episode.

In a first scenario, it is assumed that the first ATP regimen delivered in FIG. 3B is formulated (selected) from Table 1. Thus, the first ATP regimen delivered in FIG. 3B had previously been found to be "successful" and stored in Table 1 in association with one of the stored exploratory RCL values, and the current measured $RCL_E$ depicted in FIG. 3B matched that stored value. In this case, the Historical Efficacy of that ATP regimen would be decreased in Table 1.

In this first scenario, where the current $RCL_E$ depicted in FIG. 3B only matched a stored $RCL_E$ value in Table 1, the second delivered ATP regimen depicted in FIG. 3B is derived by simply selecting the next programmed baseline ATP regimen. The second delivered ATP regimen is depicted as successfully terminating the VT episode in this example of FIG. 3B and will be used to update the Table 1. If the second ATP is a failure, however, the information will be used to update the Table 2 and used to tailor subsequent ATP regimens (see below).

In a second scenario, it is assumed that the currently measured $RCL_E$ depicted in FIG. 3B matched one of the stored exploratory RCL values associated with an ATP regimen that had previously been found to be "unsuccessful" but not causing VT rate acceleration and stored in Table 2. The parameters of the first ATP regimen delivered in FIG. 3B are formulated from the stored RCL for the last two ATP regimens delivered when the same VT episode (as determined by the unique $RCL_E$ signature) was encountered previously. If the stored RCL for the last two ATP regimens during a previously detected episode showed an increasing behavior, where $RCL_{Mn}$ was greater than $RCL_M$ (n−1) by a given threshold amount, then the new ATP regimen is obtained by incrementing the number of pulses by one or in general by a fixed programmable number but keeping the CL the same as $n^{th}$ VT regimen. If, however, the RCL for the two ATP regimens did not change by a threshold amount then the new ATP regimen is obtained by keeping the number of pulses same as the $n^{th}$ ATP regimen but making the new ATP regimen more aggressive (i.e. decrementing the CL by a programmable amount e.g. 20 ms or 5% VT CL etc).

The post-delivery $RCL_{m1}$ (where m is the VT episode number and n=1) that is measured from the last ATP regimen pacing pulse $P_4$ to the VSENSE detection of the next intrinsic R-wave is used to retrieve or derive a new ATP regimen $ATP_{M2}$ that is based on last two RCLs but now the n−$1^{th}$ RCL refers to the last ATP regimen delivered during the previous episode of same VT. Consequently, the second ATP regimen for the current episode has number of pulses incremented or CL shortened depending on the difference in RCLs for the $n^{th}$ and $(n-1)^{th}$ episodes as described above.

The flow charts illustrated in FIGS. 4A and 4B and the timing diagrams of FIGS. 3A and 3B are intended to illustrate the functional operation of the algorithm of the present invention implemented into the exemplary ICD operating system 100, and should not be construed as reflective of a specific form of software, firmware and/or hardware necessary to practice the invention. It is believed that the particular form of software, firmware or hardware will be determined primarily by the particular system architecture employed in the ICD or anti-tachycardia pacemaker and by the particular detection and therapy delivery methodologies that are employed. Providing software, firmware and/or hardware to accomplish the present invention in the context of any modern implantable anti-tachycardia pacemaker or ICD, given the disclosure herein, is well within the abilities of one of skill in the art.

In the practice of the present invention, the satisfaction of VT detection criteria is followed by delivery of the exploratory ATP sequence ($ATP_E$) of pacing pulses that overdrive the VT but are not likely to terminate the VT episode. The exploratory $RCL_{Em}$ is measured following the last pacing pulse of the exploratory $ATP_E$ sequence. The steps S300-S328 of FIG. 4A illustrate the initial determination of such an exploratory $RCL_E$ upon satisfaction of VT detection criteria, the delivery of a programmed baseline ATP regimen in response to the detected VT episode, the delivery of "n" (at least one more) modified $ATP_n$ regimen(s) if the ATP regimen delivered during a pervious detection of the same episode is unsuccessful, and the accumulation of data associating the exploratory $RCL_{Em}$ with the successful or unsuccessful ATP regimen that is stored in memory in one of the tables (1, 2 and 3) of FIG. 5. The steps S330-S366 of FIG. 4B illustrate the use of successful or the avoidance of unsuccessful stored ATP regimens corresponding to stored exploratory RCL values that match (within defined tolerances) exploratory RCL values that are determined in subsequent VT episodes. Steps S310-S328 of FIG. 4A are reverted to in order to develop further modified ATP regimens when a current measured exploratory $RCL_{Em}$ does not match any stored exploratory RCLs associated in Table 1 with successful ATP regimens.

Thus, the ICD is implanted and programmed at start step S300, and the very first VT episode experienced by the patient is detected in step S302 employing any of the above-described VT detection criterion. The VT episode rate represented by $CL_T$ is also determined and temporarily stored for possible subsequent determination of VT rate acceleration. The unique VT episode count "m" is initialized to "1" in step S304. The exploratory ATP sequence is delivered in step S306, and the exploratory $RCL_{Em}$ is measured and temporarily stored in steps S308 for reference in later steps of the algorithm.

In step S310, a baseline ATP regimen of "p" pacing pulses at $CL_{mn}$ (CL of $n^{th}$ ATP sequence) is delivered, the delivered ATP regimen count "n" is set to "1", and the post-ATP regimen $RCL_{mn}$ is measured and temporarily stored for later use in the algorithm. Periodically, in responding to VT episodes, it is necessary to revert from step S362 of FIG. 4B to the delivery of a baseline ATP regimen in accordance with step S310 and selectively follow the steps S312-S328 as described further below.

In step S312, a determination of whether the delivered baseline ATP regimen is successful or unsuccessful is made. If success is achieved, then the exploratory $RCL_{Em}$ measured in step S308 is associated in step S314 with the ATP regimen (specifically the ATP regimen parameters comprising the number of delivered pacing pulses "p" and the cycle length) delivered in step S310 and stored in Table 1 and the ATP regimen Historical Efficacy of Table 1 is updated. The algorithm then advances to monitoring the VSENSE events to detect a subsequent VT episode in step S330 in FIG. 4B.

If success is not achieved as determined in step S312, then a comparison of the current VT episode rate to the VT episode rate stored in step S302 is made in step S316 to determine whether the VT has accelerated or not. If VT acceleration is determined to have occurred in step S316, then the $RCL_{Em}$ stored in step S308 is associated in step S318 with the delivered ATP regimen as having caused acceleration and stored in Table 3. The use of such a delivered ATP regimen causing acceleration to treat a future VT episode exhibiting the $RCL_E$ associated with that delivered ATP regimen is avoided in accordance with one aspect of the present invention. The algorithm then advances to S330 to determine if a shock therapy should be delivered to terminate VT or successful ATP regimen be determined starting at a new baseline therapy (S360 in FIG. 4B).

If VT acceleration has not occurred as determined in step S316, then a determination that the delivery of a further ATP regimen is programmed is made in step S320. If no further ATP regimen is programmed "ON" in step S320 (i.e., N=1 in this instance), then the $RCL_{Em}$ stored in step S308 is associated in step S322 with the ATP regimen delivered in step S310 (the $n^{th}$ ATP regimen) and stored in Table 2. In addition, the RCL for the $(n-1)^{th}$ regimen ($RCL_{Em}$ in this case) is also stored in Table 2 in association with $RCL_{Em}$). The algorithm then advances to step S342 for delivery of a C/D shock therapy or therapies until the V/T episode is terminated or all such therapies are exhausted.

If it is determined in step S320 that another ATP regimen is allowed, then a comparison is made between the most recent $RCL_{mn}$ and the preceding $RCL_{mn-1}$ measured for the same VT episode (S324). If the RCL difference is greater than a threshold amount, $RCL_{TH}$, then a subsequent ATP regimen is delivered that simply has more number of pulses (from the $n^{th}$ ATP) while maintaining the same aggressiveness (i.e. cycle length, CL) as the previously delivered ATP (S326). Alternatively, if the RCL difference is less than the threshold value, the new ATP has same number of pulses but shorter CL by a programmable value $\Delta CL$. Note that for the for the very first iteration when n=1 the RCL for the $0^{th}$ ATP regimen (i.e. exploratory sequence) and the baseline regimen are used to make decision to increment number of pulses or decrease CL for subsequently delivered ATP either during that particular detection of that episode or during a later detection of the same VT (i.e. VT having same exploratory RCL signature).

Then, steps S312 to S322 as described above are selectively repeated until one of step S312 or S316 is satisfied or it is determined in step S320 that no further ATP regimens can be delivered. In the latter case, the $RCL_{mn}$ and $RCL_{mn-1}$ are stored in Table 2 (S322) and are carried over for use in the next detected episode of the same VT. Consequently Table 2 consists of n rows each of which corresponds to a unique VT by virtue of a characteristic $RCL_{Em}$. As explained above, the next two columns of the table store RCLs for the $n^{th}$ and $n-1^{th}$ failed ATP attempt. The parameters for the $n^{th}$ failed ATP regimen are stored in the last column and these ATP parameters are used to design ATP therapy for a subsequently detected episode of the same VT. The determination of whether a currently detected episode is same as one of the prestored VTs is made by comparing the exploratory RCL for the newly detected episode with $RCL_E$s already stored in the Table 2 (S348 in FIG. 4B).

The steps S330-S366 of FIG. 4B and the steps S310-S328 of FIG. 4A are selectively followed whenever a subsequent VT episode is detected in step S330. The exploratory $ATP_E$ sequence is delivered in step S332 upon detection of each subsequent VT episode in step S330, and the $RCL_{Em}$ is measured and temporarily stored in step S334.

In step S336, the value of the measured exploratory $RCL_{Em}$ is compared to the exploratory RCL values associated with unsuccessful ATP regimens that result in VT acceleration that are stored in Table 3. If there is a match as determined in step S338, then it is undesirable to retrieve and employ the associated ATP. regimen.

In most instances, the attending physician will either program the delivery of a C/D shock therapy to convert a VT episode exhibiting a measured exploratory RCL matching an exploratory RCL entry in Table 3 or allow the delivery of another baseline ATP regimen. Therefore, the determination is made in step S340 whether the immediate delivery of a C/D shock therapy in step S342 is preferred or if any further ATP regimens are to be delivered as determined in step S360. One or more (if necessary) C/D shocks are delivered in step S342, if either the immediate delivery is preferred as determined in step S340 or no further baseline ATP therapies are to be delivered as determined in step S360. After VT termination and/or delivery of the last C/D shock in step S342, the algorithm returns to standby awaiting satisfaction of step S330. If a further baseline therapy is programmed as determined in step S362, then the next baseline therapy is loaded in step S362, and steps S310-S328 are selectively followed.

A comparison of the exploratory RCL measured in step S334 with the stored exploratory RCL values of look-up Table 1 is made in steps S344 and S346. If no match is found in step S338 between the exploratory RCL measured in step S334 and the stored exploratory RCL values of look-up Table 3, a match is attempted between $RCL_{Em}$ for the current episode and exploratory RCL stored in Table 1. If there is no match in step 346, then the exploratory $RCL_{Em}$ is matched with exploratory RCLs stored in Table 2 in steps S348 and S350.

If no match is made in step S350, then the exploratory RCL measured in step S334 does not match any of the stored RCL values in any of the look-up Tables 1-3, and the unique VT episode count "m" is incremented in step S366. In such a case, either step S342 or steps S362 and S310-S328 are followed, depending upon whether a further baseline ATP regimen is programmed in step S360. In the latter case, at least one more attempt is made to deliver an ATP regimen to terminate the VT episode and increment the database.

If a match is made in step S350, then the determination is again made in step S320 whether a further ATP regimen can be formulated and delivered. If no further ATP regimen can be formulated and delivered, then the above-described steps are followed in steps S322 and in step 342 to deliver the programmed C/D shock therapies. If a further ATP regimen can be formulated and delivered, then steps S324-S328 are selectively followed to formulate and deliver the further ATP regimen as an iteration of a previously delivered unsuccessful ATP regimen. The success or failure of the formulated ATP regimen is then determined and data stored in the look-up Tables 1-3 selectively following steps S312-S328 and steps branching therefrom again.

Returning to step S346, if a match is made between the exploratory RCL measured in step S334 with the stored RCL values of look-up Table 1, then the Historical Efficacy of the matched ATP regimen is examined in step S352. If the Historical Efficacy ($EFF_{HISTMAX}$) does not exceed an efficacy threshold ($EFF_{THRESH}$), then the unique VT episode count "m" is incremented in step S366. Again, either step S342 or steps S362 and S310-S328 are followed, depending upon whether a further baseline ATP regimen is programmed in step S360. In the latter case, at least one more ATP regimen is delivered to terminate the VT episode and increment the database. If the $EFF_{HISTMAX}$ does exceed the $EFF_{THRESH}$ as determined in step S352, then the associated ATP regimen is retrieved from Table 1 and delivered in step, S354. If the ATP regimen delivered in step S354 is successful as determined in step S356, then the Historical Efficacy of the ATP regimen is updated in step S364, and VSENSE events are monitored in step S330 to detect a further VT episode. If the ATP regimen delivered in step S354 is not successful as determined in step S356, then the Historical Efficacy of the ATP regimen is updated in step S358. In case the ATP is a failure, the determination of whether a further baseline ATP regimen is programmed is made in step S360. Again, either step S342 or steps S362 and S310-S328 are followed, depending upon whether a further baseline ATP regimen is programmed in step S360. In the latter case, at least one more attempt is made to deliver an ATP regimen to terminate the VT episode and increment the database.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of-the present invention.

What is claimed is:

1. In an implantable medical device (IMD) of the type that detects intrinsic depolarizations of a heart chamber, detects a tachycardia episode, and responds to the detected tachycardia of a heart chamber by delivering at least one anti-tachycardia pacing (ATP) regimen to the heart chamber, a method of delivering the ATP regimens further comprising:
   (a) upon detection of a tachycardia episode, delivering an exploratory ATP sequence of pacing pulses to the heart chamber to elicit a paced depolarization of the heart chamber upon delivery of at least the last delivered ATP pulse;
   (b) measuring an exploratory return cycle length (RCL) from the last delivered exploratory ATP sequence pacing pulse to the next detected intrinsic depolarization;
   (c) formulating an ATP regimen having ATP parameters formulated as a function of the measured exploratory RCL;
   (d) delivering the ATP regimen to the heart chamber;
   (e) following delivery of the ATP regimen, determining whether the tachycardia episode is terminated; and
   (f) if the tachycardia episode is determined to be terminated in step (e), storing the measured exploratory RCL used in formulating the delivered ATP regimen and storing the delivered ATP regimen as a successful ATP regimen, the stored ATP regimen being stored in association with the stored measured exploratory RCL in IMD memory.

2. The method of claim 1, wherein step (c) further comprises:
   comparing the measured exploratory RCL determined in step (b) with any previously measured, stored exploratory RCLs stored in step (f); and if the exploratory RCL measured in step (b) matches a stored exploratory RCL, retrieving the successful ATP regimen stored in association with the stored exploratory RCL from the IMD memory, the retrieved successful ATP regimen to be delivered in step (d).

3. The method of claim 2, further comprising:
(g) if the tachycardia episode is determined to not be terminated in step (e), storing the measured exploratory RCL used in formulating the delivered ATP regimen and storing the delivered ATP regimen as an unsuccessful ATP regimen, the stored ATP regimen being stored in association with the stored measured exploratory RCL in IMD memory,
whereby a database is accumulated in IMD memory comprising stored measured exploratory RCLs and stored successful and unsuccessful ATP regimens, each stored ATP regimen stored in association with a-stored exploratory RCL used to formulate the stored ATP regimen.

4. The method of claim 3, wherein:
step (a) further comprises determining a pre-ATP rate of the tachycardia prior to delivery of the exploratory ATP sequence;
step (e) further comprises:
  determining a post-ATP rate of the tachycardia following delivery of the ATP regimen; and
  comparing the post-ATP rate to the pre-ATP rate to determine if the post-ATP rate is faster or slower than the pre-ATP rate; and
step (g) further comprises:
  storing the exploratory RCL used in formulating the delivered ATP regimen and storing the delivered ATP regimen as an unsuccessful, non-accelerating, ATP regimen, the stored ATP regimen being stored in association with the stored exploratory RCL in IMD memory, if the post-ATP rate is slower or substantially the same as the pre-ATP rate; and
  storing the exploratory RCL used in formulating the delivered ATP regimen and storing the delivered ATP regimen as an unsuccessful, accelerating, ATP regimen, the stored ATP regimen stored in association with the stored exploratory RCL in IMD memory, if the post-ATP rate is faster, by a predetermined amount, than the pre-ATP rate,
whereby a database is accumulated in IMD memory comprising stored measured exploratory RCLs and stored successful and unsuccessful ATP regimens, each stored ATP regimen stored in association with a stored exploratory RCL used to formulate the ATP regimen.

5. The method of claim 4, wherein step (c) further comprises:
comparing the measured exploratory RCL determined in step (b) with the stored exploratory RCLs stored in both step (f) and step (g); and
formulating the ATP parameters of the ATP regimen to be delivered as a baseline ATP therapy if the measured exploratory RCL matches a stored exploratory RCL stored in association with an unsuccessful, accelerating, ATP regimen.

6. The method of claim 5, wherein:
step (e) further comprises:
  measuring an ATP regimen RCL from the last delivered ATP regimen pacing pulse to the next detected intrinsic depolarization; and
step (g) further comprises storing the ATP regimen RCL in IMD memory in association with the delivered ATP regimen stored as an unsuccessful, non-accelerating, ATP regimen, if the post-ATP rate is slower or substantially the same as the pre-ATP rate.

7. The method of claim 6, wherein step (c) further comprises:
comparing the measured exploratory RCL determined in step (b) with the stored exploratory RCLs stored in both step (f) and step (g); and
if the measured exploratory RCL matches a stored exploratory RCL stored in association with a stored unsuccessful, non-accelerating, ATP regimen and an associated stored ATP regimen RCL, formulating the ATP parameters of the ATP regimen to be delivered as an iteration of the ATP parameters of the unsuccessful, non-accelerating, ATP regimen and the ATP regimen RCL.

8. The method of claim 7, wherein the ATP parameters comprise an ATP cycle length and a number of ATP pulses, and step (c) further comprises:
comparing the stored ATP regimen RCL and the measured exploratory RCL; and
adjusting at least one of the ATP cycle length and the number of ATP pulses as a function of the comparison of the ATP regimen RCL to the measured exploratory RCL.

9. The method of claim 8, wherein the adjusting step comprises one of incrementing the number of ATP pulses or decrementing the ATP cycle length if the ATP regimen RCL exceeds the measured exploratory RCL by a predetermined amount.

10. The method of claim 9, wherein the adjusting step comprises the other of incrementing the number of ATP pulses or decrementing the ATP cycle length if the ATP regimen RCL does not exceed the measured exploratory RCL by a predetermined amount.

11. The method of claim 1, wherein step (f) further comprises:
if the tachycardia episode is determined to be terminated in step (e):
  classifying the delivered ATP regimen as successful;
  incrementing an historical efficacy of the delivered ATP regimen; and
  storing the delivered ATP regimen as a successful ATP regimen in association with the historical efficacy and in association with the stored exploratory RCL used in formulating the ATP regimen in IMD memory;
and wherein step (c) further comprises:
  comparing the measured exploratory RCL determined in step (b) with previous exploratory RCLs stored in step (f);
  if the exploratory RCL measured in step (b) matches at least one stored exploratory RCL, retrieving the successful ATP regimen stored in IMD memory in association with the at least one matching stored exploratory RCL from the database, the retrieved successful ATP regimen to be delivered in step (d); and
  if the exploratory RCL measured in step (b) matches more than one stored exploratory RCL, comparing the stored historical efficacies, and retrieving, from the database, a successful ATP regimen having a highest stored historical efficacy and stored in association with one of the more than one matching stored exploratory RCLs, the retrieved ATP regimen to be delivered in step (d).

12. The method of claim 11, further comprising:
(g) if the tachycardia episode is determined to not be terminated in step (e):

if the delivered ATP regimen comprises a previously stored successful ATP regimen, decrementing the historical efficacy of the stored successful ATP regimen; and if the delivered ATP regimen does not comprise a previously stored successful ATP regimen, storing the measured exploratory RCL used in formulating the delivered ATP regimen and storing the delivered ATP regimen as an unsuccessful ATP regimen, the delivered ATP regimen stored in association with the stored exploratory RCL in IMD memory, whereby a database is accumulated in IMD memory comprising stored successful and unsuccessful ATP regimens each stored in association with a stored exploratory RCL.

13. In an implantable medical device (IMD), a method of responding to a tachycardia of a heart chamber by providing anti-tachycardia pacing (ATP) therapies to the heart chamber comprising:

(a) detecting intrinsic depolarizations of the heart chamber;
(b) detecting a tachycardia episode exhibited by a series of detected intrinsic depolarizations;
(c) delivering an exploratory ATP sequence of pacing pulses to the heart chamber to elicit a paced depolarization of the heart chamber upon delivery of at least the last delivered ATP pulse;
(d) measuring the return cycle length (RCL) between the last delivered exploratory ATP sequence pacing pulse and the next detected intrinsic depolarization as a measured exploratory RCL;
(e) formulating an ATP regimen having defined ATP parameters;
(f) delivering the ATP regimen formulated in step (e) to the heart chamber to elicit a paced depolarization of the heart chamber upon delivery of each ATP pulse;
(g) following delivery of the ATP regimen, determining whether the tachycardia episode is terminated;
(h) if the tachycardia episode is determined to be terminated in step (g), classifying the delivered ATP regimen as a successful ATP regimen in association with the exploratory RCL measured in step (d);
(i) storing the exploratory RCL measured in step (d) and storing the successful ATP regimen, the stored successful ATP regimen stored in association with the stored measured exploratory RCL in IMD memory; and
(j) processing steps (a) and (b) and repeating steps (c)-(i) when a tachycardia is detected in step (b) to accumulate a database comprising at least one stored successful ATP regimen stored in IMD memory in association with at least one stored exploratory RCL, wherein repeating step (e) comprises comparing the measured exploratory RCL determined each time step (d) is repeated with each stored exploratory RCL stored in step (i) and retrieving, from the database, a successful ATP regimen stored in association with a stored exploratory RCL matching the measured exploratory RCL determined in step (d).

14. The method of claim 13, wherein:
step (h) further comprises, if the tachycardia episode is determined to not be terminated in step (g), decrementing an historical efficacy of the stored successful ATP regimen if the delivered ATP regimen comprises a previously stored successful ATP regimen; and
step (i) further comprises, if the delivered ATP regimen does not comprise a previously stored successful ATP regimen, storing the measured exploratory RCL measured in step (d) and storing the delivered ATP regimen as an unsuccessful ATP regimen in association with the stored exploratory RCL in IMD memory, whereby a database is accumulated in IMD memory comprising successful and unsuccessful ATP regimens each stored in association with a stored exploratory RCL.

15. The method of claim 13, wherein:
step (h) further comprises, if the tachycardia episode is determined to not be terminated in step (g):
    decrementing an historical efficacy of the stored successful ATP regimen if the delivered ATP regimen comprises a previously stored successful ATP regimen;
    determining if the rate of the tachycardia has accelerated;
    if tachycardia rate acceleration is determined, classifying the delivered ATP regimen as an unsuccessful, accelerating, ATP regimen in association with the measured exploratory RCL determined in step (d); and
    if tachycardia rate acceleration is not determined and if the delivered ATP regimen does not comprise a previously stored successful ATP regimen, classifying the delivered ATP regimen as an unsuccessful, non-accelerating, ATP regimen in association with the measured exploratory RCL determined in step (d); and
step (i) further comprises:
    storing the exploratory RCL determined in step (d) and storing the unsuccessful, accelerating, ATP regimen, the unsuccessful, accelerating ATP regimen stored in association with the stored measured exploratory RCL in IMD memory; and
    storing the exploratory RCL determined in step (d) and the unsuccessful, non-accelerating, ATP regimen, the unsuccessful, non-accelerating ATP regimen stored in association with the stored measured exploratory RCL in IMD memory if the delivered ATP regimen does not comprise a previously stored successful ATP regimen.

16. The method of claim 15, wherein:
step (j) further comprises processing steps (a) and (b) and repeating steps (c)-(i) when a tachycardia is detected in step (b) to accumulate a database in IMD memory comprising successful and unsuccessful, accelerating and non-accelerating, ATP regimens and associated stored exploratory RCLs, and
step (e) further comprises comparing the exploratory RCL measured in step (d) with each stored RCL, and one of:
    retrieving a successful ATP regimen from the database if the RCL determined in step (d) matches an RCL stored in association with the successful ATP regimen stored in the database; and
    retrieving an unsuccessful, non-accelerating ATP regimen from the database if the RCL determined in step (d) matches an RCL stored in association with the unsuccessful, non-accelerating, ATP regimen stored in the database.

17. The method of claim 16 wherein step (e) further comprises:
if the exploratory RCL measured in step (d) matches at least one stored exploratory RCL associated with a successful ATP regimen, retrieving the successful ATP regimen associated with the stored exploratory RCL from the database to be delivered in step (f); and
if the exploratory RCL measured in step (d) matches more than one stored exploratory RCL associated with a successful ATP regimen, comparing the stored historical efficacies, and retrieving the successful ATP regimen having the highest stored historical efficacy associated with the stored exploratory RCL from the database to be delivered in step (f).

18. The method of claim 15, wherein the ATP regimen comprises a predetermined number of ATP pulses separated by an ATP regimen cycle length and step (e) further comprises, if the measured exploratory RCL matches a stored exploratory RCL associated with an unsuccessful, non-accelerating, ATP regimen, formulating the ATP parameters of the ATP regimen to be delivered as an iteration of the ATP parameters of the unsuccessful, non-accelerating, ATP regimen by one of incrementing the number of ATP pulses or decrementing the ATP cycle length by a predetermined amount.

19. An implantable medical device (IMD) of the type that detects intrinsic depolarizations of a heart chamber, detects a tachycardia episode and responds to the detected tachycardia of a heart chamber by delivering anti-tachycardia pacing (ATP) therapies to the heart chamber comprising:

means operable upon detection of a tachycardia for delivering an exploratory ATP sequence of pacing pulses to the heart chamber to elicit a paced depolarization of the heart chamber upon delivery of at least the last delivered ATP pulse;

means for measuring the return cycle length (RCL) between the last delivered exploratory ATP sequence pacing pulse and the next detected intrinsic depolarization as a measured exploratory RCL;

formulating means for formulating an ATP regimen having ATP parameters formulated as a function of the measured exploratory RCL;

means for delivering the ATP regimen;

means for determining whether the tachycardia episode is terminated following delivery of the ATP regimen;

classifying means for classifying the delivered ATP regimen as a successful ATP regimen in association with the measured exploratory RCL if the tachycardia episode is determined to be terminated; and storing means for storing the measured exploratory RCL used in formulating the ATP regimen and for storing the successful ATP regimen, the successful ATP regimen stored in association with the stored measured exploratory RCL in IMD memory.

20. The implantable medical device of claim 19, wherein:

the formulating means further comprises means for comparing the measured exploratory RCL with each stored RCL and for retrieving a successful ATP regimen from the IMD memory when the measured exploratory RCL matches a stored RCL stored in association with the successful ATP regimen.

21. The implantable medical device of claim 20, wherein:

the classifying means is operable for classifying the delivered ATP regimen as an unsuccessful ATP regimen in association with the measured exploratory RCL if the tachycardia episode is determined to not be terminated; and the storing means is operable for storing the measured exploratory RCL used in formulating the ATP regimen and for storing the unsuccessful ATP regimen, the unsuccessful ATP regimen stored in association with the stored measured exploratory RCL in IMD memory, whereby a database is accumulated in IMD memory comprising successful and unsuccessful ATP regimens each stored in association with a stored exploratory RCL.

22. The implantable medical device of claim 21, further comprising:

means operable upon detection of a tachycardia for determining a pre-ATP rate of the tachycardia prior to delivery of the exploratory ATP sequence; and means operable if the tachycardia episode is determined to not be terminated for determining a post-ATP rate of the tachycardia following delivery of the ATP regimen; and wherein:

the classifying means is operable for classifying the delivered ATP regimen as an unsuccessful, accelerating, ATP regimen in association with the measured exploratory RCL used to formulate the ATP regimen if the post-ATP rate is faster than the pre-ATP rate and for classifying the delivered ATP regimen as an unsuccessful, non-accelerating, ATP regimen in association with the measured exploratory RCL used to formulate the ATP regimen if the pre-ATP rate is faster or the same as the post-ATP rate; and the storing means is operable for storing the measured exploratory RCL used to formulate the ATP regimen and for storing the unsuccessful, accelerating, ATP regimen in IMD memory in association with the stored measured exploratory RCL or for storing the unsuccessful, non-accelerating, ATP regimen in IMD memory in association with the stored measured exploratory RCL.

23. The implantable medical device of claim 21, further comprising:

means for determining and storing an historical efficacy of each classified successful ATP regimen stored in association with a stored exploratory RCL, the historical efficacy representing the ratio of the number of successful terminations of a tachycardia by the ATP regimen to the number of unsuccessful, non-accelerating, terminations by the same ATP regimen; and wherein:

the formulating means further comprises means for selecting a successful ATP regimen having the highest historical efficacy among stored successful ATP regimens that are stored in association with the same stored exploratory RCL that matches the measured exploratory RCL.

24. The implantable medical device of claim 19, further comprising:

storing means for storing the delivered ATP regimen as an unsuccessful ATP regimen in IMD memory in association with the stored measured exploratory RCL if the tachycardia episode is determined to not be terminated by the termination determining means;

whereby a database is accumulated in IMD memory comprising successful and unsuccessful ATP regimens each stored in association with a stored exploratory RCL.

25. The implantable medical device of claim 24, further comprising:

tachycardia rate determining means for determining a pre-ATP rate of the tachycardia prior to delivery of the exploratory ATP sequence and a post-ATP rate of the tachycardia following delivery of the ATP regimen;

and wherein the storing means is operable to store the delivered ATP regimen as an unsuccessful, non-accelerating, ATP regimen in IMD memory in association with the stored measured exploratory RCL used in formulating the ATP regimen, if the post-ATP rate is slower or substantially the same as the pre-ATP rate and is operable to store the delivered ATP regimen as an unsuccessful, accelerating, ATP regimen in IMD memory in association with the stored measured exploratory RCL used in formulating the ATP regimen, if the post-ATP rate is faster, by a predetermined amount, than the pre-ATP rate, whereby a database is accumulated in IMD memory comprising successful and unsuccessful ATP regimens each stored in association with a stored exploratory RCL.

26. The implantable medical device of claim 25, wherein the formulating means further comprises:
means for comparing the measured exploratory RCL with the stored exploratory RCLs stored in IMD memory; and
means for formulating the ATP parameters of the ATP regimen to be delivered as a baseline ATP therapy if the measured exploratory RCL matches a stored exploratory RCL stored in association with an unsuccessful, accelerating, ATP regimen.

27. The implantable medical device of claim 24, further comprising:
means for measuring an ATP regimen RCL from the last delivered ATP regimen pacing pulse to the next detected intrinsic depolarization;
tachycardia rate determining means for determining a pre-ATP rate of the tachycardia prior to delivery of the exploratory ATP sequence and a post-ATP rate of the tachycardia following delivery of the ATP regimen;
and wherein the storing means is operable to store the delivered ATP regimen as an unsuccessful, non-accelerating, ATP regimen stored in IMD memory in association with the stored measured exploratory RCL and store the ATP regimen RCL in IMD memory in association with the stored delivered ATP regimen, if the post-ATP rate is slower or substantially the same as the pre-ATP rate.

28. The implantable medical device of claim 27, wherein the formulating means further comprises means operable if the measured exploratory RCL matches a stored exploratory RCL stored in association with an unsuccessful, non-accelerating, ATP regimen for formulating the ATP parameters of the ATP regimen to be delivered as an iteration of the ATP parameters of the unsuccessful, non-accelerating, ATP regimen and its associated stored ATP regimen RCL.

29. The implantable medical device of claim 28, wherein the ATP parameters comprise an ATP cycle length and a number of ATP pulses, and the formulating means further comprises means for adjusting at least one of the ATP cycle length and the number of ATP pulses as a function of the comparison of the stored ATP regimen RCL to the measured exploratory RCL.

30. The implantable medical device of claim 29, wherein the adjusting comprises one of incrementing the number of ATP pulses or decrementing the ATP cycle length if the ATP regimen RCL exceeds the measured exploratory RCL by a predetermined amount.

31. The implantable medical device of claim 30, wherein the adjusting comprises the other of incrementing the number of ATP pulses or decrementing the ATP cycle length if the ATP regimen RCL does not exceed the measured exploratory RCL by a predetermined amount.

32. The implantable medical device of claim 19, further comprising:
means for determining whether the tachycardia episode is terminated following delivery of the ATP regimen; and
means operable if the tachycardia episode is determined to be terminated for classifying the delivered ATP regimen as successful for incrementing an historical efficacy of the delivered ATP regimen, and storing the delivered ATP regimen as a successful ATP regimen in association with the historical efficacy and the stored measured exploratory RCL in IMD memory;
and wherein the formulating means further comprises:
means for comparing the measured exploratory RCL with stored exploratory RCLs;
means operable if the measured exploratory RCL matches at least one stored exploratory RCL for retrieving a successful ATP regimen stored in association with the matching stored exploratory RCL from the IMD memory to be delivered to the heart; and
means operable if the measured exploratory RCL matches more than one stored exploratory RCL for comparing the stored historical efficacies and for retrieving a successful ATP regimen having the highest stored historical efficacy and stored in association with the matching stored exploratory RCL from the IMD memory to be delivered to the heart.

33. The implantable medical device of claim 32, further comprising:
means for decrementing the historical efficacy of the stored successful ATP regimen if the delivered ATP regimen comprises a previously stored successful ATP regimen and has not terminated the tachycardia episode; and
means for storing the delivered ATP regimen as an unsuccessful ATP regimen in IMD memory in association with the stored measured exploratory RCL, if the delivered ATP regimen does not comprise a previously stored successful ATP regimen
whereby a database is accumulated in IMD memory comprising successful and unsuccessful ATP regimens each stored in association with a stored exploratory RCL.

34. In an implantable medical device (IMD), apparatus that responds to a tachycardia of a heart chamber by providing anti-tachycardia pacing (ATP) therapies to the heart chamber comprising:
detecting means for detecting intrinsic depolarizations of the heart chamber;
tachycardia detecting means for detecting a tachycardia episode exhibited by a series of detected intrinsic depolarizations;
pacing pulse delivery means for delivering pacing pulses to the heart chamber;
means for operating the pacing pulse delivery means to deliver an exploratory ATP sequence of pacing pulses to the heart chamber to elicit a paced depolarization of the heart chamber upon delivery of at least the last delivered ATP pulse;
return cycle length (RCL) determining means for measuring an exploratory RCL between the last delivered exploratory ATP sequence pacing pulse and the next detected intrinsic depolarization;
ATP regimen formulating means for formulating an ATP regimen having defined ATP parameters;
means for operating the pacing pulse delivery means to deliver the formulated ATP regimen of ATP pulses to the heart chamber;
termination determining means for determining whether the tachycardia episode is terminated or not terminated following delivery of the ATP regimen;
classifying means for classifying the delivered ATP regimen as a successful ATP regimen in association with the measured exploratory RCL if the tachycardia episode is determined to be terminated; and
storing means for storing the measured exploratory RCL and for storing the successful ATP regimen in IMD memory in association with the stored measured exploratory RCL, and
wherein the ATP regimen formulating means comprises means for comparing each subsequently measured exploratory RCL with each stored RCL stored in IMD memory in association with a stored successful ATP regimen, and means for retrieving a stored successful ATP regimen if the measured exploratory RCL matches a RCL stored in IMD memory in association with the successful ATP regimen.

35. The implantable medical device of claim 34, wherein:

the classifying means further comprises means for classifying the delivered ATP regimen as an unsuccessful ATP regimen in association with the measured exploratory RCL if the tachycardia episode is determined to not be terminated; and the storing means further comprises means for storing the measured exploratory RCL and for storing the unsuccessful ATP regimen in IMD memory in association with the stored measured exploratory RCL.

36. The implantable medical device of claim 35, wherein the classifying means further comprises:

tachycardia acceleration determining means for determining if the rate of the tachycardia has accelerated if the tachycardia episode is determined to not be terminated, means for classifying the delivered ATP regimen as an unsuccessful, accelerating, ATP regimen in association with the measured exploratory RCL if acceleration is determined; and means for classifying the delivered ATP regimen as an unsuccessful, non-accelerating, ATP regimen in association with the measured exploratory RCL if acceleration is not determined.

37. The implantable medical device of claim 36, wherein the storing means further comprises means for storing the unsuccessful, accelerating, ATP regimen in IMD memory in association with the stored measured exploratory RCL or the unsuccessful, non-accelerating, ATP regimen in IMD memory in association with the stored measured exploratory RCL.

* * * * *